US012606591B2

(12) United States Patent
Lenna et al.

(10) Patent No.: US 12,606,591 B2
(45) Date of Patent: Apr. 21, 2026

(54) PROCESS FOR THE PREPARATION OF DROSPIRENONE AS A FINE POWDER THROUGH A DOUBLE CHANGE OF CRYSTALLINE FORM

(71) Applicant: INDUSTRIALE CHIMICA S.R.L., Milan (IT)

(72) Inventors: Roberto Lenna, S. Giorgio su Legnano (IT); Michele Baldrighi, Milan (IT)

(73) Assignee: INDUSTRIALE CHIMICA S.R.L., Milan (IT)

( * ) Notice: Subject to any disclaimer, the term of this patent is extended or adjusted under 35 U.S.C. 154(b) by 402 days.

(21) Appl. No.: 18/553,923

(22) PCT Filed: Apr. 8, 2022

(86) PCT No.: PCT/IB2022/053322
§ 371 (c)(1),
(2) Date: Oct. 4, 2023

(87) PCT Pub. No.: WO2022/215048
PCT Pub. Date: Oct. 13, 2022

(65) Prior Publication Data

US 2024/0199684 A1 Jun. 20, 2024

(30) Foreign Application Priority Data

Apr. 8, 2021 (IT) ........................ 102021000008834

(51) Int. Cl.
*C07J 53/00* (2006.01)

(52) U.S. Cl.
CPC .................................. *C07J 53/008* (2013.01)

(58) Field of Classification Search
CPC ..................................................... C07J 53/008
USPC ........................................................... 540/23
See application file for complete search history.

(56) References Cited

U.S. PATENT DOCUMENTS

2011/0144071 A1 6/2011 Grawe et al.

FOREIGN PATENT DOCUMENTS

| | | | |
|---|---|---|---|
| EP | 1214076 B1 | 11/2003 | |
| EP | 2415778 A1 * | 2/2012 | .......... C07D 307/94 |
| IT | 102004901251570 | 4/2006 | |

OTHER PUBLICATIONS

International Search Report for PCT Application No. PCT/IB2022/053322 dated Jun. 29, 2022 (12 pages).
Norbert Rasenack et al., “Micron-Size Drug Particles: Common and Novel Micronization Techniques”, Pharmaceutical Development and Technology, Jan. 2004, vol. 9, No. 1, pp. 1-13.
Henry Laurent et al., “Synthesis and Activitities of Anti-Aldosterones”, J. steroid Biochem, Jan. 1983, vol. 19, No. 1, pp. 771-776.

* cited by examiner

*Primary Examiner* — Niloofar Rahmani
(74) *Attorney, Agent, or Firm* — Leason Ellis LLP

(57) ABSTRACT

The present invention refers to a process for the industrial-scale preparation of 17β-hydroxy-6β,7β; 15β,16β-dimethylene-3-oxo-17α-pregn-4-ene-21-carboxylic acid γ-lactone, known by the common name of Drospirenone, in the form of a fine powder without the use of mechanical grinding or micronization techniques, but rather exploiting a double change of crystalline form, from Crystalline Form I to Crystalline Form II and from Crystalline Form II to Crystalline Form I. The invention also refers to the new Crystalline Form II of Drospirenone obtained in the process.

11 Claims, 8 Drawing Sheets

PROCESS FOR THE PREPARATION OF DROSPIRENONE AS A FINE POWDER THROUGH A DOUBLE CHANGE OF CRYSTALLINE FORM

CROSS-REFERENCE TO RELATED APPLICATIONS

This application is a U.S. National Stage Application under 35 U.S.C. § 371 of International Patent Application No. PCT/IB2022/053322, filed Apr. 8, 2022, which claims priority to Italian Patent Application No. 102021000008834 filed Apr. 8, 2021, the contents of which are each hereby incorporated by reference in their respective entireties.

FIELD OF THE INVENTION

The present invention refers to the field of active ingredients for pharmaceutical use, and in particular to a process for the industrial-scale preparation of 17β-hydroxy-6β, 7β; 15, 16β-dimethylene-3-oxo-17α-pregn-4-ene-21-carboxylic acid γ-lactone, known by the common name of Drospirenone, in the form of a fine powder without the use of mechanical grinding or micronization techniques, but exploiting the formation of a new solid form.

The invention also refers to the new solid form of Drospirenone obtained through the process.

STATE OF THE ART

Drospirenone is a steroid widely used in combined oral contraceptives (COCs) and in postmenopausal hormone replacement therapy in combination with 17-β-estradiol as a progestin.

The structural formula of Drospirenone is as follows:

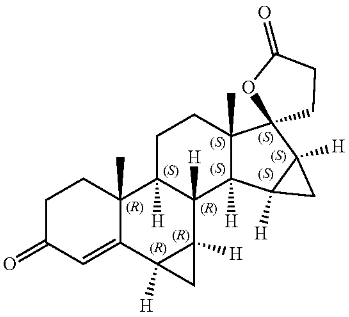

Drospirenone has been known in the literature since the 1980s (J Steroid Biochem, 19 (1), 771-76, 1983). To date, only one crystalline form of Drospirenone is known which has a octahedral habit, as shown in FIG. 1, and which will be defined in the remainder of the description as "Drospirenone Crystalline Form I"; the only other known solid form of the compound is the amorphous form, as indicated in the Italian patent no. 1357209 B1 in the name of the present Applicant.

The advantage of using Drospirenone in micronized form in pharmaceutical compositions is known from EP 1214076 B1.

Pharmaceutical Development and Technology vol. 9, No 1, pp. 1-13 (2004) discusses various techniques for reducing the particle size of a pharmaceutical active ingredients (these ingredients are indicated in the sector with the abbreviation "API") that can be used in pharmaceutical compositions.

These techniques range from mechanical grinding methods to spray-drying, crystallization with supercritical fluids, precipitation by solvent change.

The most used and most practical technique in the pharmaceutical field is the mechanical grinding of the APIs, which however has a series of drawbacks, as well explained on page 3 of the Pharmaceutical Development and Technology article cited above. The main of these problems is the partial or total alteration of the crystalline structure (amorphization, transformation into different solid forms) due to the mechanical stress to which the powders are subjected during grinding/micronization. These uncontrolled changes in crystalline form are undesirable for pharmaceutical industry processes, as they lead to issues of API content uniformity in the dosage form (typically tablets) due to unpredictable mechanical interactions with excipients, or to possible return over time to the starting crystalline form (when this is more thermodynamically stable), and in general to an altered bioavailability of the API.

The object of the present invention is to provide a method of reducing the particle size of crystalline Drospirenone in Crystalline Form I without using mechanical grinding methods.

SUMMARY OF THE INVENTION

This object is achieved with the present invention, which in its first aspect consists of a process for the direct production of Drospirenone having fine particle size through a double change of crystalline form:

1) from Crystalline Form I to Crystalline Form II; and
2) from Crystalline Form II to Crystalline Form I, comprising the following steps:

a) preparing a suspension of a solid form of Drospirenone Crystalline Form I in a mixture of acetone and diisopropyl ether;
b) cooling the suspension to a temperature equal to or lower than −5° C.;
c) stirring the suspension at the temperature of point b) until the formation of Crystalline Form II needle-like crystals is observed;
d) filtering the suspension at a temperature equal to or lower than −5° C.;
e) drying the obtained crystalline solid at a temperature above +5° C., thereby obtaining Drospirenone Crystalline Form I having fine particle size.

In a preferred embodiment, the process comprises the addition of a seed of Drospirenone Crystalline Form II to the suspension of step c).

In its second aspect, the invention relates to the new Drospirenone Crystalline Form II, produced through the process described above.

DESCRIPTION OF THE FIGURES

The invention will be described with reference to the Figures, wherein.

DETAILED DESCRIPTION OF THE INVENTION

As known in crystallography, crystalline solids are characterized by a crystalline lattice or structure that describe the geometry of the crystal unit cell and the arrangement of the atoms in the cell, and by a crystalline habit describing instead the external morphology of the crystal.

In the remainder of the description and the claims the definitions "Crystalline Form I" and "Crystalline Form II" are used to define the crystalline structures of the different Drospirenone forms of the process of the invention, and the definitions "octahedral habit" and "needle-like habit" are used to define the external appearance of crystals; however, as is well known, there is no certain two-way relationship between crystalline structure and crystalline habit.

In the present case, the needle-like habit is not indicative of the presence of Crystalline Form I or II.

Crystalline Form I is characterized by the presence, in an X-ray powder diffraction spectrum (XRPD), of two intense peaks at angles 2θ of 12.30° and 17.35° (FIG. 3), while Crystalline Form II is characterized by the presence in an XRPD spectrum of three intense peaks at angles 2θ of 8.90°, 16.75° and 18.56° (FIG. 4); all these angles, as well as those reported below, are to be intended with the usual approximation of +0.2° 2θ typical of this technique.

Moreover, the terms "fine powder" or "fine particle size" means herein a powder with $X_{90}$ lower than 50 μm; in a cumulative volumetric distribution, $X_{90}$ indicates the equivalent sphere diameter value defining the 90th percentile of the total volume of the particles making up the sample.

In its first aspect, the invention consists of a process for the direct production of Drospirenone having fine particle size through a double change of crystalline form:

1) from Crystalline Form I to Crystalline Form II; and 2) from Crystalline Form II to Crystalline Form I.

In detail, the process consists of the steps described below.

Step a) may be carried out according to two alternative methods, a1) and a2).

Figure 1A:
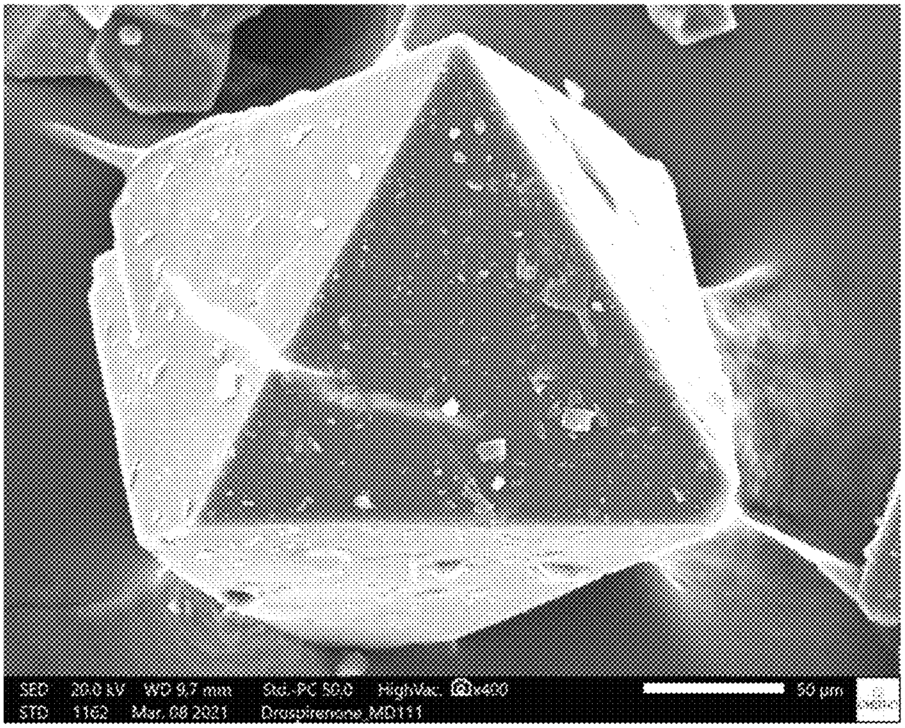
FIG. 1 shows two photographs at different magnification obtained by scanning electron microscope (SEM) of Drospirenone crystals in the Crystalline Form I of the prior art.
Figure 1B:
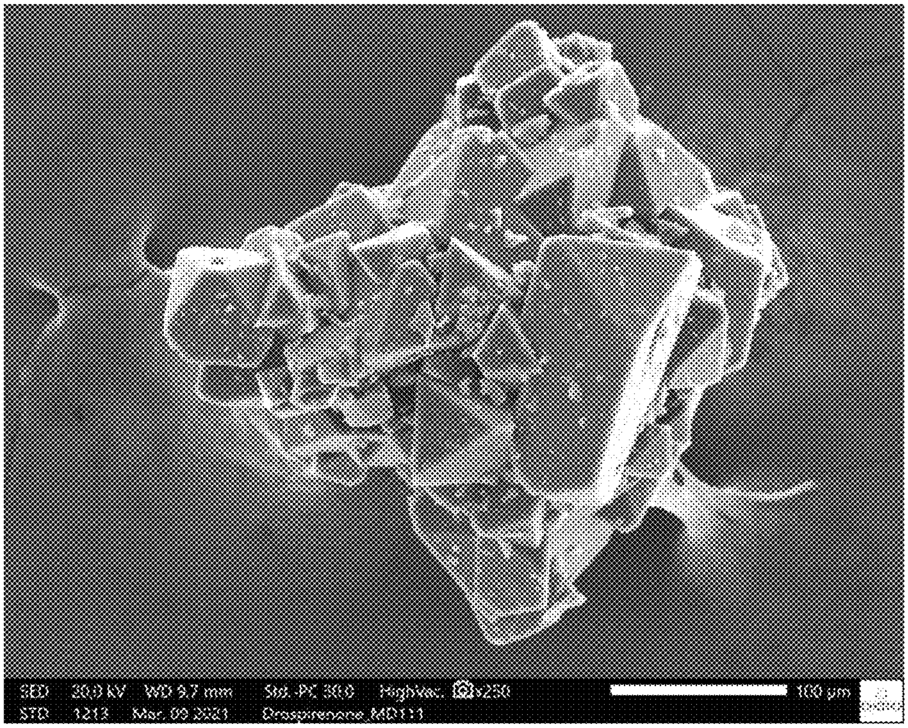

According to method a1), a suspension is prepared by mixing powders of a solid form of Drospirenone with a mixture of acetone and diisopropyl ether (commonly referred to as isopropyl ether), at a temperature comprised between 0 and 45° C. This starting solid form consists of powders of Crystalline Form I of the API; this known form of Drospirenone generally has a characteristic octahedral habit which is shown, at two different magnifications, in the two SEM images of FIG. 1. The Drospirenone used is of pharmaceutical grade, while acetone and isopropyl ether are of standard quality, with purity higher than 99%, and are preferably filtered before use to eliminate any physical impurities possibly present. The suspension is preferably stirred to separate the powder granules and disperse them in the solvent.

In an alternative embodiment, the suspension may be prepared according to method a2) by dissolving and recrystallizing a solid form of Drospirenone (in this case it is also possible to use amorphous Drospirenone as starting material). According to this alternative method, solid Drospirenone is solubilized in acetone by reflux heating; the solution thus obtained is then cooled to a temperature comprised between 40 and 45° C.; isopropyl ether is then added to this cooled solution, an addition which determines the crystallization of Drospirenone in the Crystalline Form I with formation of the suspension of step a); the whole procedure is carried out under stirring.

The preparation of the suspension by dissolution and recrystallization of the API leads to a suspension with grains of more homogeneous size that accelerate the transition to Crystalline Form II.

In step b) the suspension obtained as described above, according to any one of the two methods for carrying out step a), is cooled to a temperature of ≤−5° C.

In step c), the suspension of step b) is kept under stirring at the indicated temperature until the change of crystal morphology from octahedral to needle-like is observed, which has been noted to accompany the transformation of the crystalline structure from Crystalline Form I to Crystalline Form II, as confirmable by XRPD analysis.

This step may be carried out according to two alternative methods, c1) and c2).

According to method c1), this step is carried out by letting the spontaneous transformation into Crystalline Form II to take place, which takes place in a time comprised between 0.5 and 48 hours. Preferably, according to this method, the suspension is kept under stirring at a temperature comprised between −10 and −5° C. for a time comprised between 0.5 and 24 hours.

In the preferred embodiment of the process, step c) is carried out according to method c2) by adding to the suspension a small amount of Drospirenone Crystalline Form II obtained in a previous preparation, which acts as a trigger for the desired transformation; under these conditions, and operating at a temperature comprised between −10 and −5° C. under stirring, the transformation is typically complete in a time comprised between 0.5 and 2 hours. In this preferred embodiment, a further addition of isopropyl ether to the suspension can also optionally be carried out in step c2).

The transformation of the initial powders (both in case method c1 and in case method c2 is adopted) can be monitored using dedicated commercial automatic instruments, such as the ParticleView V19 probe (Mettler Toledo) and related images acquisition and processing software iC PVM (Mettler Toledo); this probe is connected to a high-magnification micro-camera with the possibility of continuously recording images, and allows to observe the formation and transformation of crystals in solution in real time.

At the same time, it is possible to confirm the change of crystalline form by analyzing the wet solid using XRPD analysis.

Figure 2A:
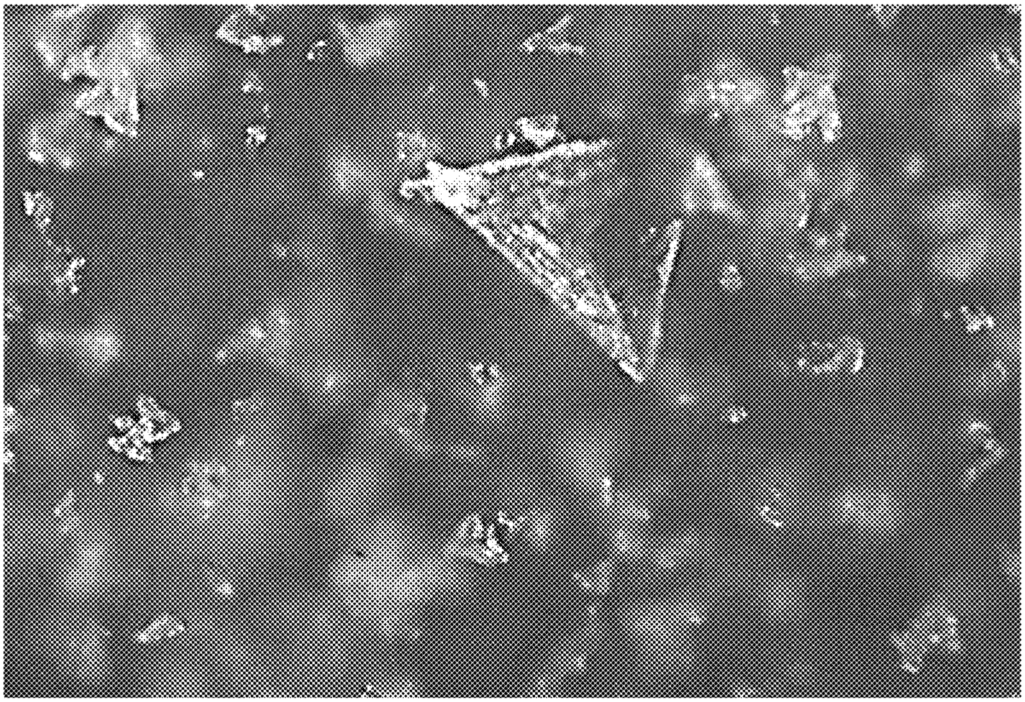
FIG. 2 shows two photographs of Drospirenone obtained with the ParticleView V19 probe before (FIG. 2*a*) and after (FIG. 2*b*) the transformation from Crystalline Form I to Crystalline Form II.
Figure 2B:
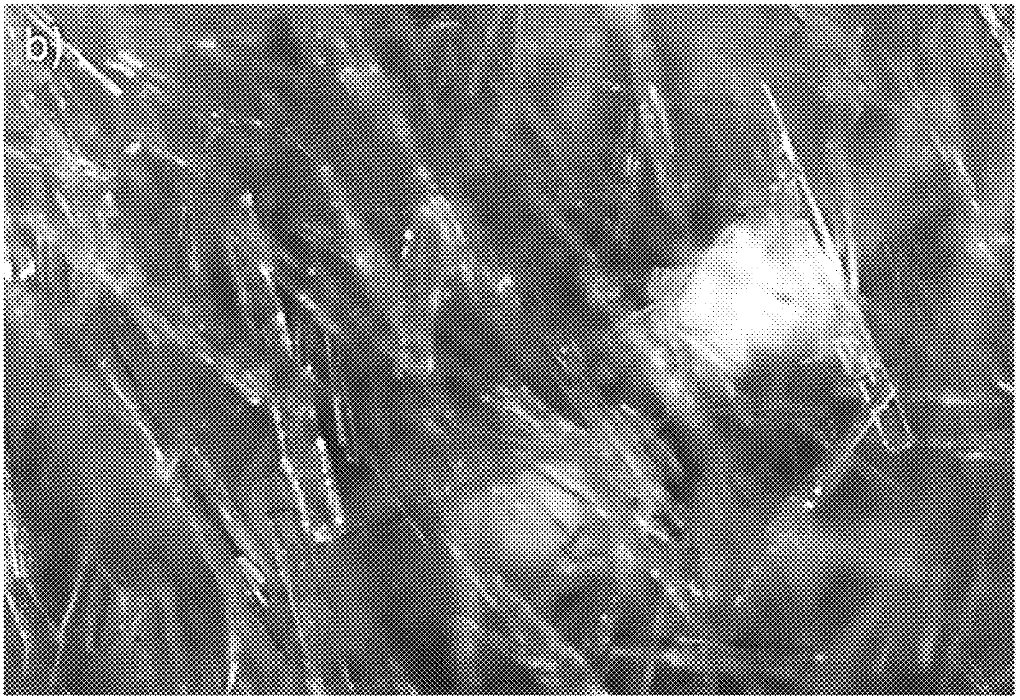

FIG. 2 shows two photographs of Drospirenone obtained with the Particle View V19 probe before (FIG. 2*a*) and after (FIG. 2*b*) the transformation from Crystalline Form I to Crystalline Form II which occurs during the realization of step c). In the upper portion of the figure, the starting Drospirenone having Crystalline Form I (octahedral habit) is shown, while in the lower portion of the figure the appearance of the needle-like crystals that are produced in this passage is visible.

After the transformation of the crystals in suspension is complete, these are recovered through step d) consisting in filtering the suspension at a temperature equal to or lower than −5° C., preferably comprised between −10 and −5° C. By submitting to XRPD analysis these still wet crystals, it was verified that they are in Crystalline Form II.

In the last step of the process, e), the crystalline solid product thus obtained is dried at a temperature above +5° C., preferably at a temperature of 40-50° C., operating at a pressure lower than the ambient one.

The drying of step e) produces the solid-solid transformation of Drospirenone which returns from Crystalline Form II to Crystalline Form I, while maintaining the needle-like habit.

With the change in crystalline form that occurs in this step, from Crystalline Form II to Crystalline Form I, a spontaneous crushing of the crystals occurs with a reduction in their size and the obtainment of API particles having a particle size suitable for use in the formulations for drug administration, without the need to resort to grinding.

In its second aspect, the invention relates to Drospirenone Crystalline Form II which is produced as an intermediate of the process.

The industrial utility of this new crystalline form, as previously described, is to allow the obtainment of Drospirenone Crystalline Form I with a particle size lower than that obtained with processes of the prior art, and which is already suitable for the production of pharmaceutical formulations without requiring mechanical treatments to reduce the size.

Figure 3:
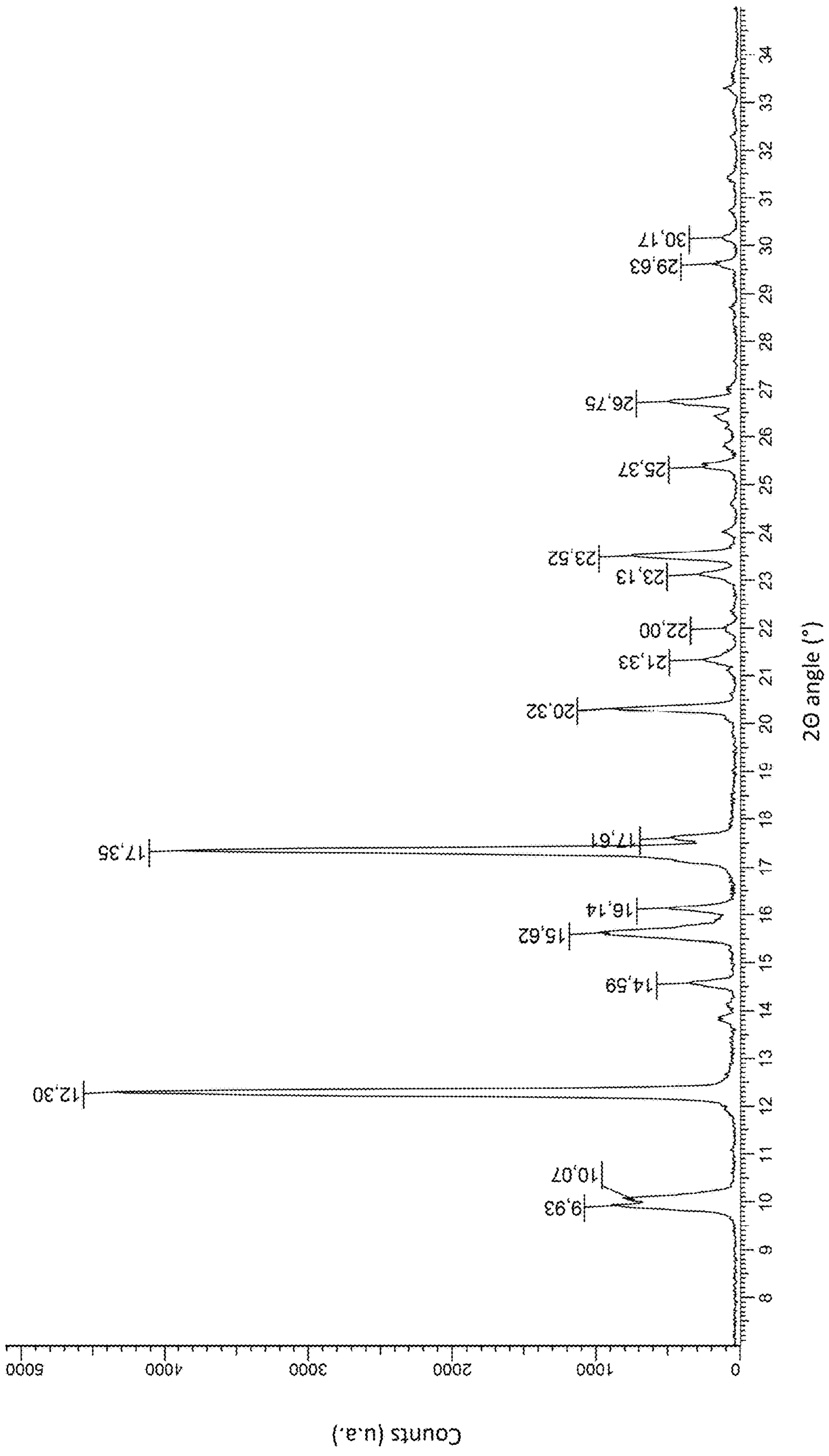
FIG. 3 shows the XRPD spectrum of Drospirenone Crystalline Form I powders.
Figure 4:
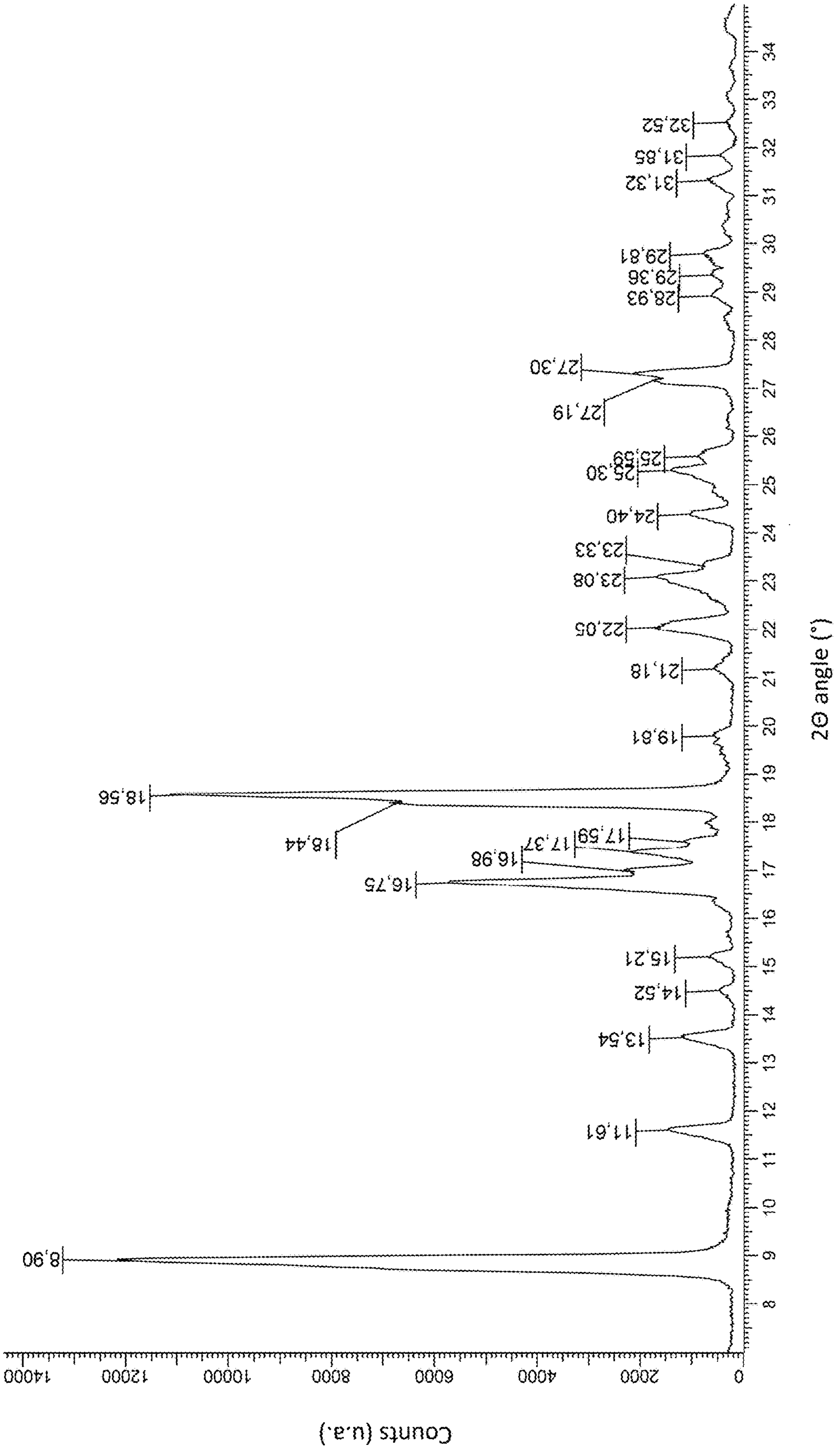
FIG. 4 shows the XRPD spectrum of Drospirenone Crystalline Form II powders.

FIGS. 3 and 4 reproduce an X-ray powder diffraction spectrum (XRPD) of known Drospirenone Crystalline Form I and of Crystalline Form II of the present invention, respectively (the spectrum of Crystalline Form I is reported for comparison purposes).

The spectrum of the Crystalline Form II powders was obtained from wet powders obtained after step d) of the process, because, as mentioned, the drying transforms this form back into the known Crystalline Form I.

Below are the listings of the main peaks of the XRPD spectra of the two crystalline forms with their relative intensities. The angular positions of the diffraction peaks are intended to have an uncertainty of ±0.2 2θ°).

| Crystalline Form II (FIG. 4) | | Crystalline Form I (FIG. 3) | |
|---|---|---|---|
| 2θ Angle (°) | Relative Intensity (%) | 2θ Angle (°) | Relative Intensity (%) |
| 8.90 | 100.00 | 9.93 | 19 |
| 11.61 | 10.60 | 10.07 | 16 |
| 13.54 | 8.50 | 12.30 | 100 |
| 14.52 | 2.40 | 14.59 | 7 |
| 15.21 | 4.00 | 15.62 | 21 |
| 16.75 | 46.80 | 16.14 | 10 |
| 16.98 | 16.10 | 17.35 | 89 |
| 17.37 | 16.30 | 17.61 | 10 |
| 17.59 | 7.10 | 20.32 | 20 |
| 18.44 | 54.60 | 21.33 | 5 |
| 18.56 | 91.10 | 22.00 | 2 |
| 19.81 | 2.50 | 23.13 | 6 |
| 21.18 | 2.70 | 23.52 | 17 |
| 22.05 | 11.90 | 25.37 | 5 |
| 23.08 | 12.20 | 26.75 | 11 |
| 23.33 | 4.40 | 29.63 | 3 |
| 24.40 | 6.70 | 30.17 | 2 |

-continued

| Crystalline Form II (FIG. 4) | | Crystalline Form I (FIG. 3) | |
|---|---|---|---|
| 2θ Angle (°) | Relative Intensity (%) | 2θ Angle (°) | Relative Intensity (%) |
| 25.30 | 10.00 | | |
| 25.59 | 5.60 | | |
| 27.19 | 12.70 | | |
| 27.30 | 16.00 | | |
| 28.93 | 3.40 | | |
| 29.36 | 3.10 | | |
| 29.81 | 4.70 | | |
| 31.32 | 3.80 | | |
| 31.85 | 2.40 | | |
| 32.52 | 1.20 | | |

Figure 5:
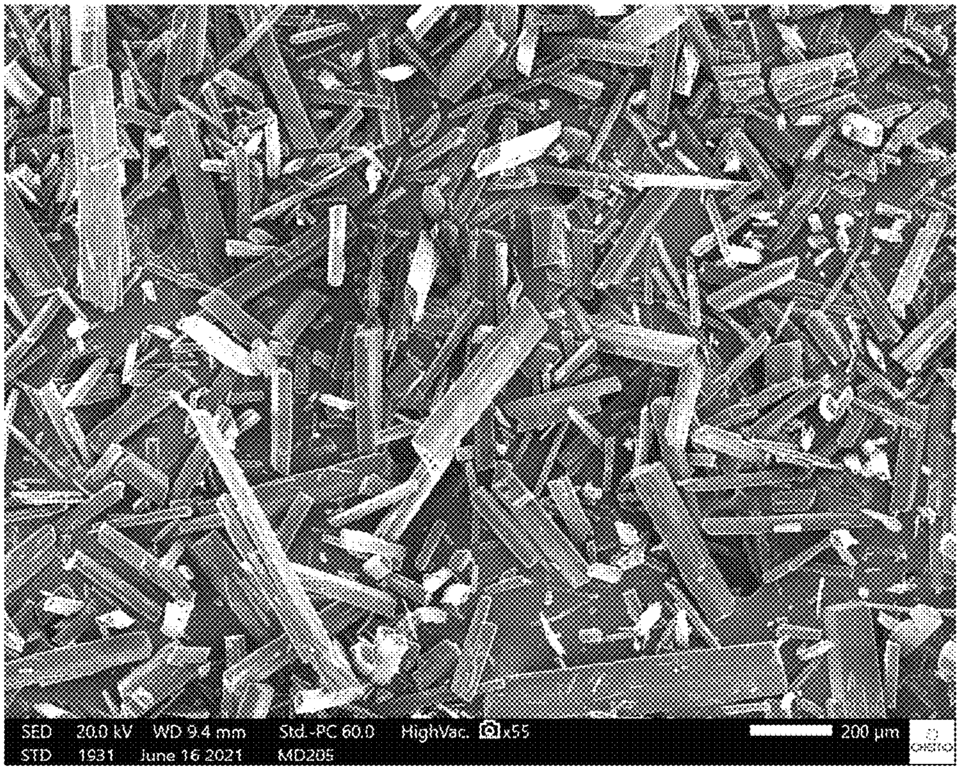
FIG. 5 shows a photograph, obtained using a scanning electron microscope (SEM), of Drospirenone crystals in the final form of the invention, Crystalline Form I, after retransformation from Crystalline Form II.
Figure 6:
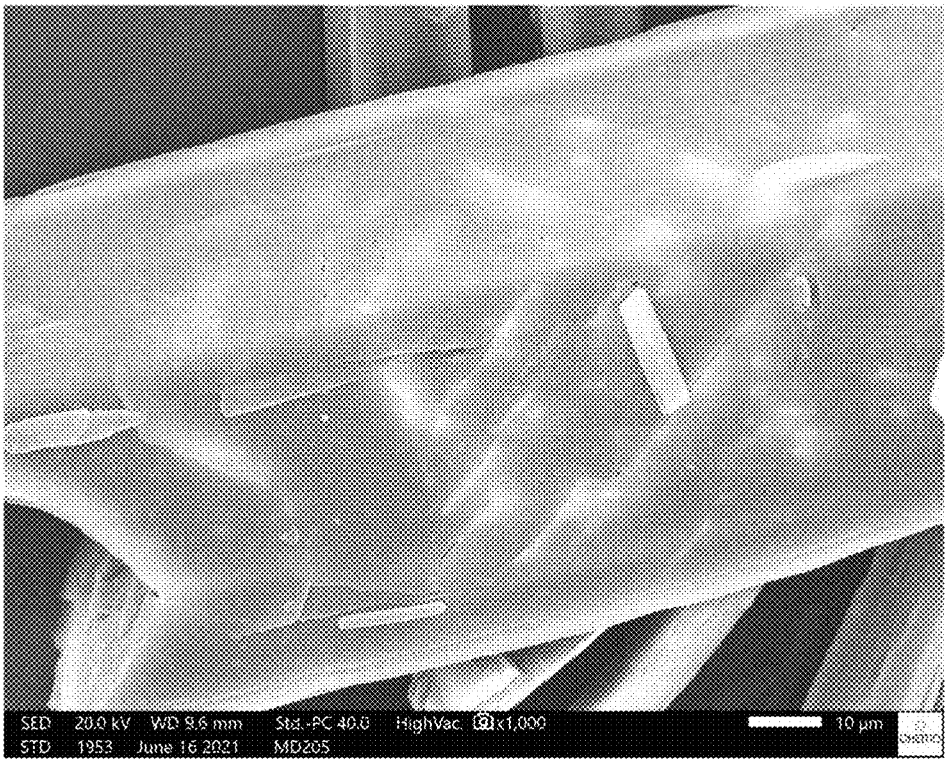
FIGS. 6 to 8 show enlarged details of FIG. 5.
Figure 7:
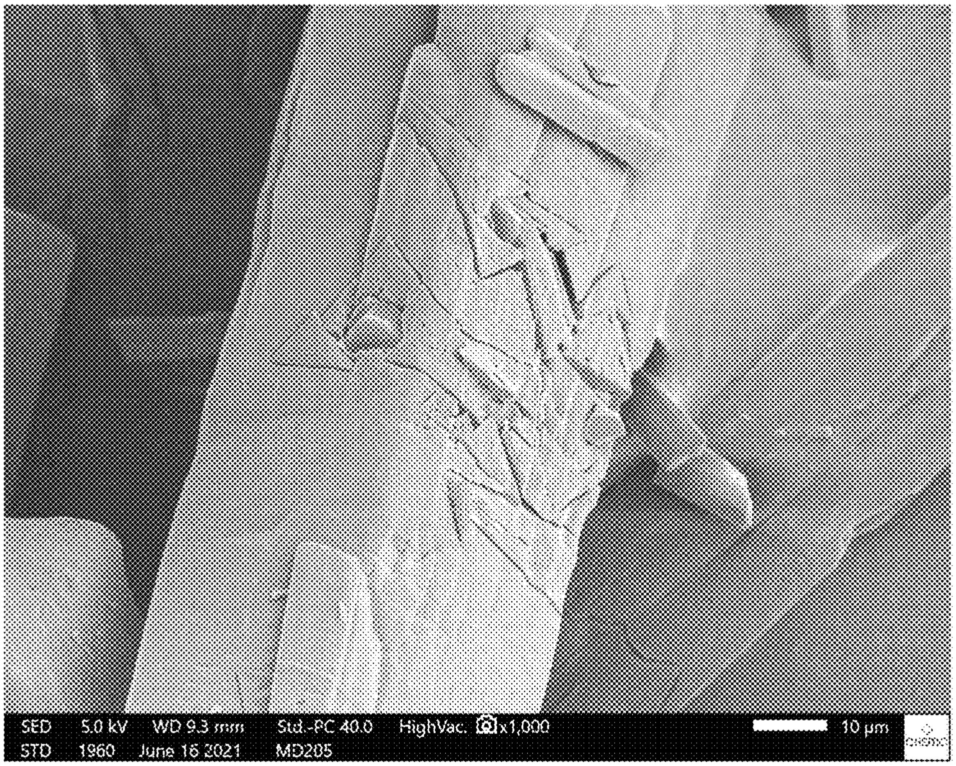
Figure 8:
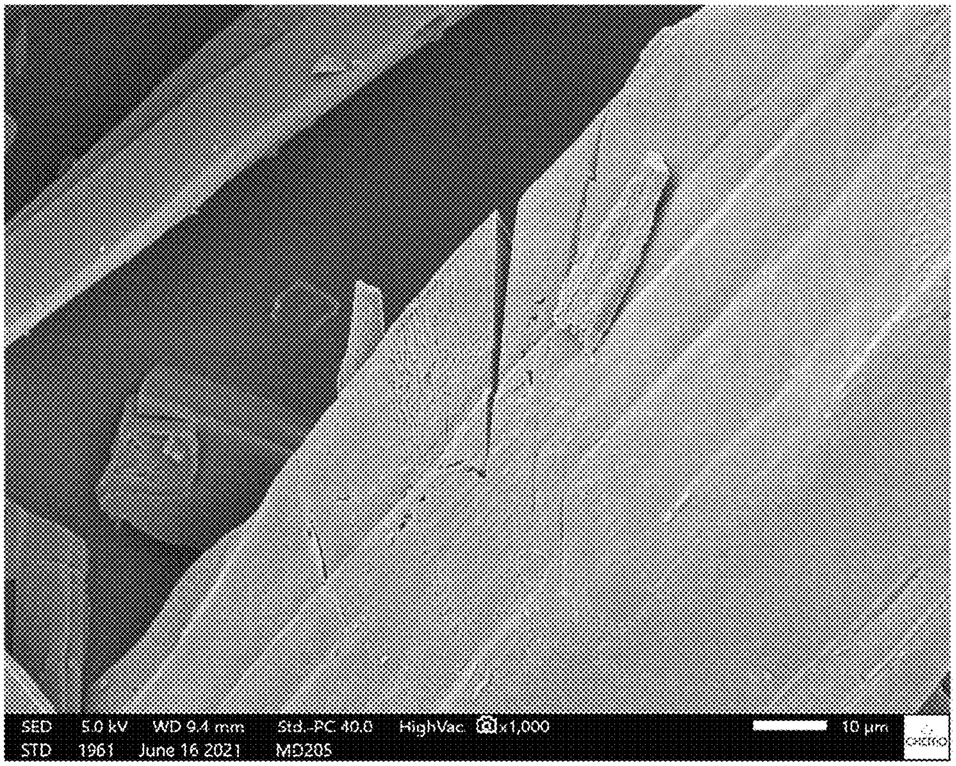

By exploiting the double change of crystalline form, from Crystalline Form I to Crystalline Form II and, again, from Crystalline Form II to Crystalline Form I, microfractures are generated in the crystals which make additional mechanical treatments to reduce particle size superfluous. The phenomenon is illustrated in FIGS. 5-8. FIG. 5 shows a scanning electron microscope (SEM) photograph of Drospirenone Crystalline Form I crystals after retransformation from Crystalline Form II; FIGS. 6, 7 and 8 show electron microscope photographs of single crystals of FIG. 5, obtained at higher magnification and highlighting the presence of fracture lines.

The invention will be further illustrated by the following examples.

Instruments, Methods, and Experimental Conditions

Images of Drospirenone crystals during crystallization were acquired using the ParticleView V19 probe (Mettler Toledo) and related image acquisition and processing software iC PVM (Mettler Toledo).

DRX analyzes were performed using a Bruker D2 Phaser diffractometer (2nd ed.) operating with a copper anode X-ray source ($\lambda = K\alpha_{1,2} = 1.54184$ Å). Kβ radiation was removed using a Nickel filter. The X-ray detector is a linear solid-state detector, LINXEYE model. The samples were loaded as a thin layer on a "zero background" silicon sample holder and analyzed in the range 7-35° 2θ with increments of 0.02° 2θ and acquisition time of 4 s/° 2θ, rotating the sample holder during the analyses.

Electron microscopy images were acquired using a SEM JSM-IT200 (Jeol) microscope operated in high vacuum at 20 kV and with a SED detector. The samples were deposited on the SEM support using a double-sided adhesive and conductive carbon film and were metallized with gold before analysis.

The powders particle size was measured using a Helos laser particle size analyzer equipped with a Quixel disperser (instrument and disperser manufactured and sold by the company Sympatec GmbH of Clausthal-Zellerfeld, Germany), using ultrapure milli-Q water as the dispersing medium. The sample was first dispersed in milli-Q water by adding a few drops of Tween® 80 (polyethylene glycol sorbitan monooleate, sold by Merck) and placed in a sonicating bath for 5 min, then the suspension was added to the dispersing medium loaded into the instrument until an optical density value OD=4-15% is obtained. The measurement (30 s background +30 s measurement) was performed by operating under continuous sonication with the recirculation pump set at 20%.

The water used in carrying out the experimental tests (apart from the particle size measurements) is to be intended as pure, unless otherwise indicated.

The organic solvents used in the tests are to be intended of "technical" grade, unless otherwise indicated.

The reagents and catalysts used in the tests are to be intended of commercial quality, unless otherwise indicated.

Example 1

This example refers to the process of the invention in its most general embodiment (without addition of a Drospirenone Crystalline Form II seed).

250 g of Drospirenone Crystalline Form I and 1700 mL of acetone are loaded into a 3 L jacketed reactor with anchor stirrer, condenser, temperature probe, and liquid heating and cooling system.

The mixture is put under stirring, heated to reflux, and kept under stirring until the solid is completely dissolved.

The solution is cooled to 40-45° C., then 600 mL of isopropyl ether are added. The formation of octahedral crystals is observed.

The mixture is left under stirring for 10 min, then it is cooled to −5° C.

The suspension is left under stirring. When, after 22 hours, the transformation from octahedral to needle-like crystals is observed, the mixture is left under stirring at −5° C. for a further 24 hours.

The suspension is filtered under vacuum, Drospirenone (white solid) is recovered as Crystalline Form II (DRX analysis performed on the wet sample) which is stored at T<5° C.

The DRX spectrum of Drospirenone Crystalline Form II obtained in this example is shown in FIG. 4, and is characterized by diffraction peaks at angular positions of: 8.9°, 11.6°, 13.5°, 14.5°, 15.2°, 16.8°, 17.0°, 17.4°, 17.6°, 18.4°, 18.6°, 19.8°, 21.2°, 22.1°, 23.1°, 23.3°, 24.4°, 25.3°, 25.6°, 27.2°, 27.3°, 28.9°, 29.4°, 29.8°, 31.3°, 31.9° e 32.5°±0.2° 2θ.

Example 2

This example refers to the process of the invention carried out by adding a seed of Drospirenone Crystalline Form II to a suspension obtained by adding powders of Crystalline Form I to the solvent (steps sequence a1→b→c2→d→e).

In a 100 mL reactor, 5 g of Drospirenone Crystalline Form I, 27.5 mL of acetone and 35.0 mL of isopropyl ether are loaded at a temperature comprised between 20 and 25° C.

The suspension thus obtained is put under stirring and cooled to −5° C. for 10 minutes.

50 mg of Drospirenone Crystalline Form II obtained in Example 1 are added, and the suspension is kept under stirring for 2 hours at −5° C.

The suspension is filtered and Drospirenone (white solid) is recovered.

The wet solid is dried under vacuum at 50° C. for 16 hours.

The XRPD diffractogram of the obtained solid (shown in FIG. 3) corresponds to that of the known Crystalline Form I, with peaks at the angular positions reported above, while the crystalline habit corresponds to the needle-like one of Crystalline Form II Example 3

This example refers to the process of the invention carried out by adding a seed of Drospirenone Crystalline Form II to a suspension of Crystalline Form I obtained by crystallization from a solution (sequence of steps a2→b→c2→d→e).

100 g of Drospirenone Crystalline Form I and 550 mL of acetone are loaded into a 3 L jacketed reactor with anchor stirrer, condenser, temperature probe, and liquid heating and cooling system.

The suspension is put under stirring and heated to reflux, keeping under stirring until the solid is completely dissolved.

The solution is cooled to 40-45° C., then 240 mL of isopropyl ether are added. The formation of octahedral crystals is observed.

The suspension thus obtained is cooled to −5° C., left under stirring for 10 minutes, then 1.0 g of Drospirenone Crystalline Form II (obtained in Example 1) is added and stirring is continued for 30 min.

A further 1160 mL of isopropyl ether are added (keeping the temperature of the mixture constantly ≤3° C.) and keeping the suspension under stirring for 2 hours, while keeping the internal temperature comprised between −5° C. and −10° C.

The suspension is filtered, Drospirenone (white solid) is recovered.

The XRPD spectrum of the freshly filtered wet solid corresponds to that obtained in Example 1 (FIG. 4).

The wet solid is dried under vacuum at 50° C. for 6 hours.

The solid obtained is subjected again to DRX analysis; the spectrum corresponds to that of Drospirenone Crystalline Form I, but the powder maintains the crystalline habit of Crystalline Form II as apparent from the comparison between FIG. 2*b* and FIG. 5.

Figure 9:
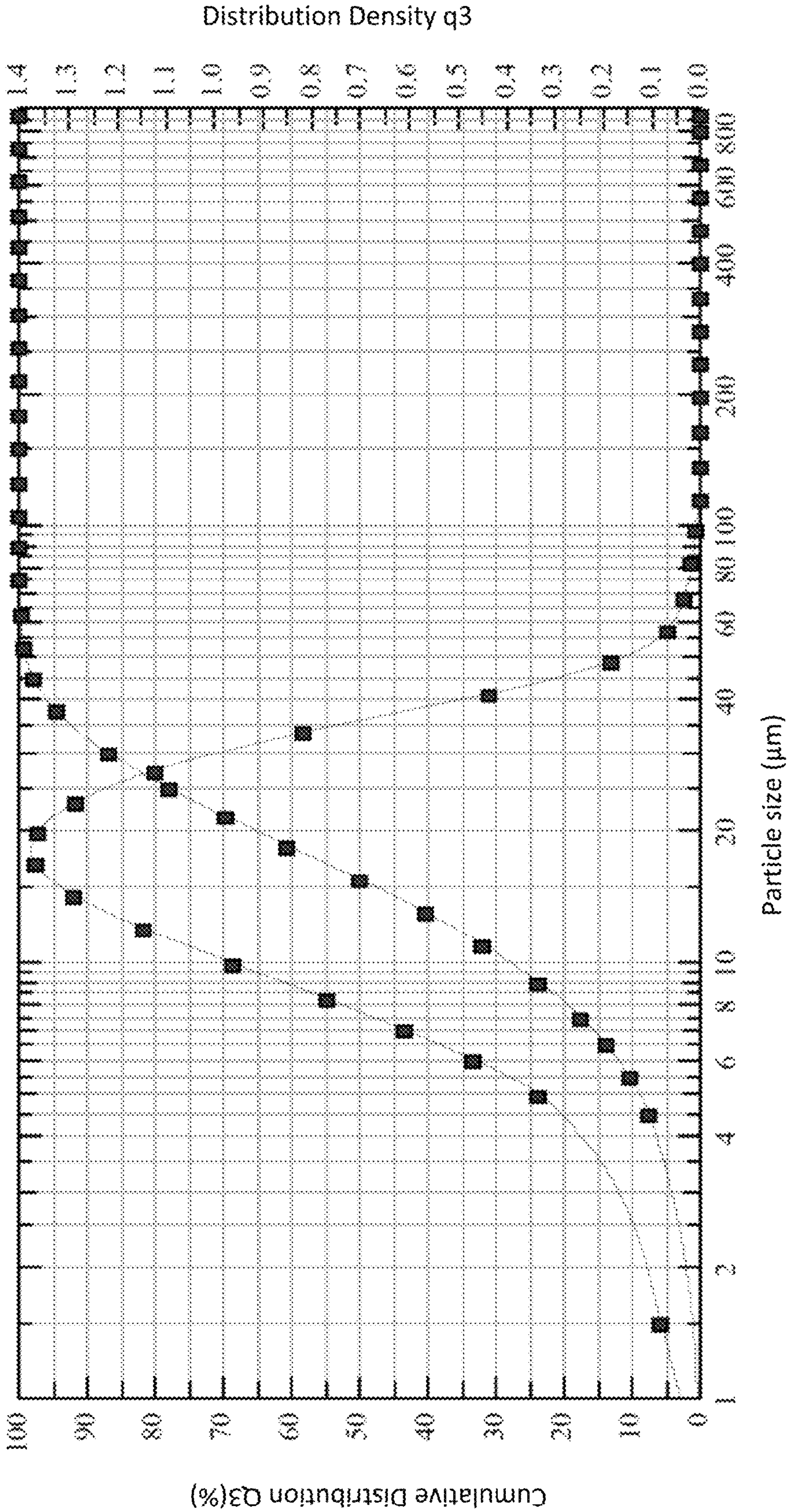
FIG. 9 shows a dimensional distribution graph of Drospirenone powders in the final form of the invention, Crystalline Form I, after retransformation from Crystalline Form II.

A particle size measurement is carried out on this powder; the curve obtained is reproduced in FIG. 9 and shows the obtainment of a fine powder. In particular, the bell curve (to which the vertical scale on the right of the figure refers) shows that the maximum of the particle size distribution of the sample particles is comprised between 15 and 20 μm and that all particles have a size lower than 110 μm (as also confirmed by the cumulative curve to which the vertical scale on the left of the figure refers).

Example 4 (Comparative)

In this example, the process of the invention is reproduced only in part, and the transformation from Crystalline Form I to Crystalline Form II does not occur.

5 g of Drospirenone and 27.3 mL of acetone are loaded into a 100 mL EasyMax reactor.

The suspension is put under stirring and heated to reflux until complete dissolution.

The solution is cooled to 40-45° ° C., then 34.7 mL of isopropyl ether are added.

The suspension thus obtained is cooled to 0° C., kept under stirring for 10 minutes, then filtered.

The solid is then dried in a vacuum oven at 45° C. for 16 hours.

The XRPD diffractogram of the obtained solid corresponds to that of the known Crystalline Form I, with peaks at the angular positions reported above.

Figure 10:
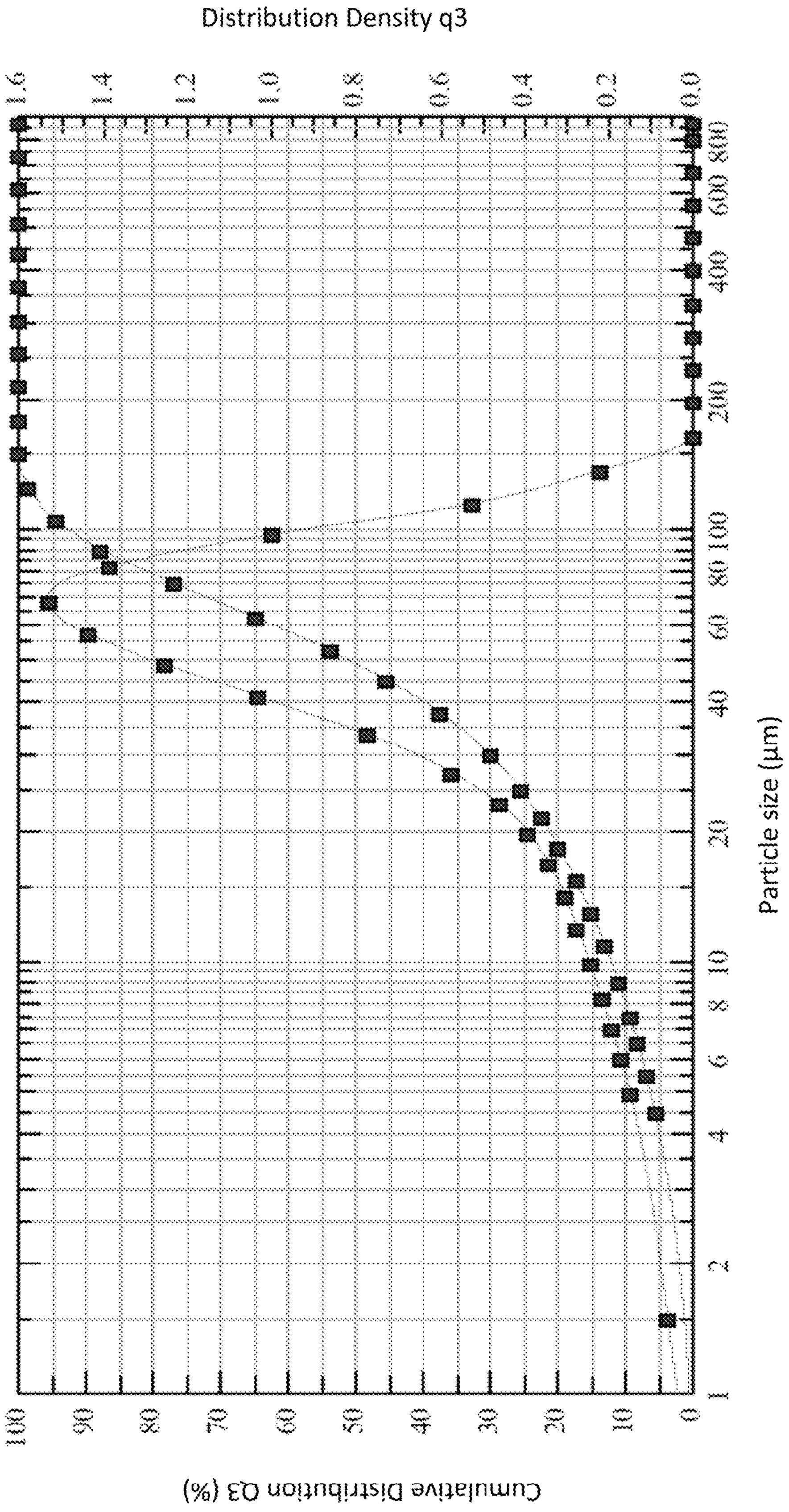
FIG. 10 shows a graph of the dimensional distribution of Drospirenone powders in Crystalline Form I obtained according to Example 3 for comparison purposes.

A particle size measurement is carried out on this powder; the results are graphically shown in FIG. 10, which shows the obtainment of a coarser powder than that obtained according to the procedure of Example 2, with the peak of the sample particles size distribution at about 70 μm and particles having size of over 150 μm.

The invention claimed is:

1. A process for the production of 17β-hydroxy-6β,7β; 15β,16β-dimethylene-3-oxo-17α-pregn-4-ene-21-carboxylic acid γ-lactone (Drospirenone) having fine particle size, characterized by a $X_{90}$ value lower than 50 μm, through a double change of crystalline form:

1) From Crystalline Form I to Crystalline Form II, characterized by the presence in an XRPD spectrum of peaks at angles of 8.90°, 16.75° and 18.56°±0.2° 2θ; and 2) From Crystalline Form II to Crystalline Form I, characterized by the presence in an XRPD spectrum of peaks at angles of 12.30° and 17.35°±0.2° 2θ.

2. The process according to claim 1, comprising the following steps:

a) preparing a suspension of a solid form of Drospirenone Crystalline Form I in a mixture of acetone and diisopropyl ether;

b) cooling the suspension to a temperature equal to or lower than −5° C.;

c) stirring the suspension at the temperature of step b) until the formation of Crystalline Form II crystals is observed;

d) filtering the suspension at a temperature equal to or lower than −5° C.;

e) drying the obtained crystalline solid at a temperature above +5° C., thereby obtaining Drospirenone in Crystalline Form I having fine particle size.

3. The process according to claim 2, wherein step a) is carried out according to a method a1) by suspending powders of Drospirenone Crystalline Form I in a mixture of acetone and diisopropyl ether.

4. The process according to claim 2, wherein step a) is carried out according to a method a2) by dissolving powders of Drospirenone, Crystalline Form I or amorphous form, in acetone under reflux conditions, cooling the obtained solution to a temperature comprised between 4° and 45° C., and adding diisopropyl ether to the cooled solution, carrying out the whole procedure under stirring.

5. The process according to claim 2, wherein step c) is carried out according to a method c1) by allowing the spontaneous transformation into Crystalline Form II to take place in a time comprised between 0.5 and 48 hours.

6. The process according to claim 5, wherein step c) is carried out according to method c1) at a temperature comprised between −10 and −5° C. for a time comprised between 0.5 and 24 hours.

7. The process according to claim 2, wherein step c) is carried out according to a method c2) by adding a seed of Drospirenone Crystalline Form II to the suspension of step b).

8. The process according to claim 7, wherein step c) according to method c2) is carried out at a temperature comprised between −10 and −5° C. for a time comprised between 0.5 and 2 hours.

9. The process according to claim 7, wherein a further addition of diisopropyl ether to the suspension is carried out.

10. The process according to claim 2, wherein step e) is carried out at a temperature comprised between 4° and 50° C. operating at a pressure lower than ambient pressure.

11. Drospirenone Crystalline Form II characterized by an X-ray diffractogram showing diffraction peaks at angular positions of 8.9°, 11.6°, 13.5°, 16.8°, 18.4°, 18.6°, 23.1°, 24.4° and 27.3°±0.2° 2θ.

* * * * *